Figure 1:
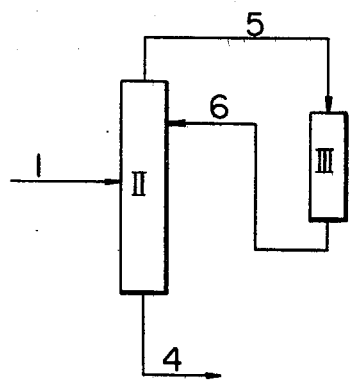

United States Patent [19]

Yoshida et al.

[11] Patent Number: 4,465,853

[45] Date of Patent: Aug. 14, 1984

[54] METHOD FOR ISOMERIZING DIACETOXYBUTENES

[75] Inventors: Yoshinori Yoshida; Hironobu Shinohara, both of Yokohama, Japan

[73] Assignee: Japan Synthetic Rubber Co., Ltd., Tokyo, Japan

[21] Appl. No.: 444,384

[22] Filed: Nov. 26, 1982

Related U.S. Application Data

[63] Continuation of Ser. No. 156,257, Jun. 3, 1980.

[30] Foreign Application Priority Data

Jun. 13, 1979 [JP] Japan .................................. 54-73552
Feb. 6, 1980 [JP] Japan .................................. 55-12533

[51] Int. Cl.$^3$ .......................... C07C 67/02; B01D 3/34
[52] U.S. Cl. ..................................... 560/262; 560/261; 560/263; 560/264; 203/29; 203/38; 203/DIG. 6
[58] Field of Search .................. 560/262, 261; 203/29, 203/38, DIG. 6

[56] References Cited

U.S. PATENT DOCUMENTS

| | | | |
|---|---|---|---|
| 2,575,896 | 11/1951 | Smith et al. ......................... | 560/262 |
| 2,846,485 | 8/1958 | Meason et al. ........................ | 203/29 |
| 3,007,853 | 11/1961 | Patron et al. ......................... | 203/29 |
| 4,044,050 | 8/1977 | Kurkov ............................... | 560/262 |

OTHER PUBLICATIONS

Kressman, Advances in Ion Exchange, Manufact. Chemist, Nov. 1956, pp. 454–458.

*Primary Examiner*—Natalie Trousof
*Assistant Examiner*—Bruce D. Gray
*Attorney, Agent, or Firm*—Oblon, Fisher, Spivak, McClelland & Maier

[57] ABSTRACT

3,4-Diacetoxybutene-1 can be easily isomerized into 1,4-diacetoxybutene-2 by contacting it with a cation exchange resin. This method is capable of providing an excellent reaction result and is free of the problem of corrosion of apparatus as well as the problem of formation of by-products. When acetic acid is present in said isomerization operation, the reaction rate is increased. Further, combination of this isomerization method with separation of 1,4-diacetoxybutene-2 from 3,4-diacetoxybutene-1 by distillation enables production of high-purity 1,4-diacetoxybutene-2 at a high efficiency.

9 Claims, 3 Drawing Figures

METHOD FOR ISOMERIZING DIACETOXYBUTENES

This is a continuation of application Ser. No. 156,257, filed June 3, 1980.

This invention relates to a method for the isomerization of 3,4-diacetoxybutene-1 (hereinafter referred to as 3,4-DABE). The invention also relates to a continuous and efficient method for the production of 1,4-diacetoxybutene-2 (hereinafter referred to as 1,4-DABE) by isomerization.

Heretofore, a variety of methods have been proposed for the production of diacetoxybutenes through reaction of butadiene, acetic acid and oxygen in the gas or liquid phase in the presence of a catalyst comprising essentially a noble metal such as palladium, platinum or rhodium. It is known that, in this acetoxylation reaction, the proportions of 1,4-DABE and 3,4-DABE produced are varied depending on the type of the catalyst used and the reaction conditions.

Of these diacetoxybutenes, 1,4-DABE can be converted into industrially useful compounds such as 1,4-butanediol, tetrahydrofuran, etc., by a suitable treatment such as hydrogenation, hydrolysis, etc.

However, 3,4-DABE cannot be used as the starting material for the preparation of 1,4-butanediol or tetrahydrofuran, so that studies are being made for elevating the yield of 1,4-DABE in said acetoxylation reaction, but production of a certain amount of 3,4-DABE as a by-product is unavoidable in the available processes. Therefore, efforts are being made for finding a method of isomerizing 3,4-DABE into 1,4-DABE at a high efficiency.

As the method of isomerization of 3,4-DABE, there is known a method by which the isomerization is performed in the gas phase by using alumina as an isomerization catalyst, but this method involves problems in selectivity and yield. As the isomerization method in the liquid phase, there have been proposed a method using sulfuric acid (method 1), a method using a palladium or platinum compound (method 2) and a method using a copper compound (method 3). Of these methods, method 1 has such problems as low yield, production of a high-boiling matter as a by-product, corrosion of apparatus, etc., while method 2 involves the problem of loss of the expensive noble metals during separation of the catalyst from the product, and it is also said that there takes place inactivation of the catalyst due to metallization of the palladium compound used as the catalyst. On the other hand, method 3 has problems in separation of the catalyst, yield of the product, and the like.

Thus, many attempts for the isomerization of 3,4-DABE have been made as mentioned above but have respective problems and no industrially advantageous methods have been found.

In order to selectively isomerize 3,4-DABE in a mixture of 1,4-DABE and 3,4-DABE into 1,4-DABE, first of all, 3,4-DABE and 1,4-DABE are separated with high purities from each other and the 3,4-DABE is then isomerized into 1,4-DABE, but this method requires a distillation tower with a great number of plates for distillation-separation of 3,4-DABE from 1,4-DABE which are very close to each other in gas-liquid equilibrium relation, and in addition, this method is disadvantageous in respect of energy consumption. Also, this isomerization reaction is an equilibrium reaction where the equilibrium is reached around the ratio of 1,4-DABE:3,4-DABE=70:30 at a temperature of around 100° C., and also a separating operation is again required after the isomerization reaction is completed. Therefore, said method is very complicated.

As a result of extensive research on the isomerization of 3,4-DABE, it has been found that an excellent reaction result can be obtained when 3,4-DABE is isomerized into 1,4-DABE with a cation exchange resin which is an easily available material, that this method is free of problems of corrosion of apparatus and formation of by-products and also that separation of the catalyst (cation exchange resin) is very easy. It has also been found that the reaction rate increases amazingly when this reaction is carried out in the presence of acetic acid.

The present inventors have also conducted research on an industrially advantageous method for the production of 1,4-DABE by isomerizing 3,4-DABE and it has consequently been found that 1,4-DABE can be produced continuously in an increased yield by a process which comprises supplying into a distillation tower a mixture comprising 1,4-DABE and 3,4-DABE, distillation-fractionating from the top of the tower a mixture containing 3,4-DABE in a higher ratio than that in the equilibrum composition at the isomerization reacton temperature of diacetoxybutenes, supplying the distillate into an isomerization reactor containing a cation exchange resin, circulating the isomerized mixture into the distillation tower and withdrawing the 1,4-DABE with the desired high purity from the tower bottom. This process has many other advantages as mentioned below. Separation of 3,4-DABE from 1,4-DABE is relatively easy because it is not necessary to make that purity of 3,4-DABE unnecessarily high, and also no further equipment is required for separation of the reaction mixture after the isomerization reaction. Moreover, if acetic acid is present during the isomerization reaction, the reaction rate can be maintained at a high level and there takes place almost no decrease of activity with the lapse of time. When acetic acid is previously incorporated into the mixture comprising 1,4-DABE and 3,4-DABE, it is possible to produce 1,4-DABE at a high efficiency by a process which comprises distillation-fractionating a substantial portion of the acetic acid in a distillation tower, supplying the distillate to a distillation tower for distillation-fractionating 3,4-DABE, feeding the resultant distillate to an isomerization reactor to effect isomerization, circulating the isomerized mixture into a distillation tower for distillation-fractionating 3,4-DABE and withdrawing high-purity 1,4-DABE from the tower bottom, In this case, it is not required to perfectly remove the acetic acid in the first distillation tower, so that in the production of diacetoxybutenes by reacting butadiene, acetic acid and oxygen in the presence of a solid catalyst, the reaction mixture comprising acetic acid, 1,4-DABE and 3,4-DABE can be supplied to the isomerization reaction step without perfectly removing the acetic acid, thus enabling very efficient production of 1,4-DABE.

An object of this invention is to provide a method for producing 1,4-DABE advantageously in industry.

Another object of this invention is to provide a method for isomerizing 3,4-DABE into 1,4-DABE at a high efficiency.

Other objects and advantages of this invention will become apparent from the following description.

According to this invention, there is provided a method for the isomerization of 3,4-DABE which comprises contacting 3,4-DABE with a cation exchange resin in the presence or absence of acetic acid to produce 1,4-DABE.

According to this invention, there is also provided a method for producing 1,4-DABE which comprises supplying a mixture comprising 1,4-DABE and 3,4-DABE into a distillation tower, distillation-fractionating from the tower top a mixture comprising 3,4-DABE in a higher ratio than that in the equilibrium composition of diacetoxybutenes at the isomerization reaction temperature, supplying the distillate into an isomerization reactor containing a cation exchange resin to effect isomerization in the liquid phase, further supplying the isomerization reaction mixture to the above distillation tower and continuously discharging the high-purity 1,4-DABE from the tower bottom.

This invention further provides a method for producing 1,4-DABE which comprises supplying a mixture comprising 1,4-DABE, 3,4-DABE and acetic acid to a first distillation tower, distillation-fractionating a substantial portion of acetic acid from the tower top while supplying to a second distillation tower the mixture comprising 1,4-DABE, 3,4-DABE and acetic acid obtained from the tower bottom, distillation-fractionating the acetic acid and a mixture comprising 3,4-DABE in a higher ratio than that in the equilibrium composition at the isomerization temperature, supplying the distillate to an isomerization reactor containing a cation exchange resin to effect isomerizaton in the liquid phase, circulating the whole of the isomerization reaction mixture into the first distillation tower or supplying a part of said reaction mixture into the second distillation tower while circulating the remainder into the first distillation tower, and continuously discharging high-purity 1,4-DABE from the bottom of the second distillation tower.

The starting material 3,4-DABE used in this invention may contain an organic solvent or solvents, water and the like in such quantities as will not obstruct the operations in the method of this invention.

The cation exchange resin used for the isomerization reaction of 3,4-DABE in the method of this invention may be of any type, but it is preferred to use a strongly acidic cation exchange resin. Among the strongly acidic cation exchange resins usable in this invention, most useful are strongly acidic cation exchange resins of sulfonic acid type comprising a styrene-divinylbenzene copolymer as a matrix, and such resins may be of either so-called gel type or porous type.

The ratio of the cation exchange resin to 3,4-DABE is not critical but in view of reaction rate, economy, etc., said ratio is preferably within the range of from 0.001–10% by weight.

The isomerization reactor used in this invention may be suitably selected from fixed-bed reactor, flow type reactor, heterogeneous liquid-phase batch type reactor, etc.

The isomerization reaction temperature is not critical but in view of thermal stability of cation exchange resin, reaction rate and catalyst life, it is preferable that said reaction temperature is within the range of 30°–150° C., more preferably 50°–120° C.

The contact time between the starting material and the cation exchange resin may be varied depending upon the concentration of 3,4-DABE in the starting material, the target concentration of 3,4-DABE after isomerization, the reaction temperature, the amount of the cation exchange resin and the like. Therefore, the contact time, the concentration of 3,4-DABE in the starting material, the isomerization rate, the reaction temperature, the amount of the cation exchange resin used and the like may be suitably selected taking economy into consideration.

The reaction rate can be increased by incorporating acetic acid. Therefore, if acetic acid is previously present in the starting material, the isomerization reaction of 3,4-DABE can be accomplished favorably, but when acetic acid is not present in the starting material and hence neither present in the isomerization reaction, it is preferable to add a suitable quantity of acetic acid prior to performing the isomerization reaction. Acetic acid, which has thus been found to be an isomerization reaction promotor, can enhance the reaction rate about 15% even when only 1 part by weight of acetic acid is added to 100 parts by weight of 3,4-DABE. Addition of 200 parts by weight of acetic acid provides an approximately 300% enhancement of reaction rate. The amount of acetic acid added is determined by taking into consideration the above-mentioned results as well as the economical factors such as separation of acetic acid after the isomerization reaction, isomerization throughput and catalyst life, but usually it is recommendable to add acetic acid in a proportion of 0.1–2,000 parts, preferably 10–1,000 parts, by weight per 100 parts by weight of 3,4-DABE. It is, of course, possible to add the same in a larger amount if economy is disregarded.

Since acetic acid thus has an activity-enhancing effect, when 3,4-DABE to be isomerized is separated from the reaction mixture obtained, for example, through acetoxylation of butadiene, the acetic acid may be left contained in the 3,4-DABE, and hence it is unnecessary to strictly separate acetic acid from 3,4-DABE by distillation.

Since the cation exchange resin used in this invention acts as a catalyst and its catalytic activity can be easily recovered by a hydrochloric acid treatment, the use of said resin is very advantageous in the isomerization process.

As the starting material in this invention there may be used a mixture comprising 1,4-DABE and 3,4-DABE, obtained by acetoxylating butadiene in the presence of a solid catalyst and then removing butadiene, water and the like from the acetoxylation mixture.

When said mixture used as starting material contains no acetic acid or contains it in an amount within the above-mentioned range, said mixture is forwarded to a second distillation tower to fractionate a mixture containing 3,4-DABE in a higher ratio than that in the equilibrium composition at the isomerization temperature. When acetic acid is contained in a larger amount than the above-mentioned range, the mixture is first sent to the first distillation tower to distillation-fractionate a substantial portion thereof and the bottom stream of said tower is sent to the second distillation tower. The amount of acetic acid fractionated in the first distillation tower is suitably changed depending on the amount of acetic acid required in the isomerization reaction. Therefore, the distillation operation conditions in the first distillation tower are varied depending on the starting material composition, the amount of acetic acid to be removed and the like, but usually the distillation is performed under reduced pressure or under pressure of up to 10 kg/cm$^2$, preferably 0.1–5 kg/cm$^2$, and at a bottom temperature of not more than 220° C., preferably 40°–180° C. in view of polymerizability of diacetoxybutenes. The number of plates in the distillation tower and the reflux ratio are also greatly variable, depending upon the separating conditions and other factors, and hence cannot be uniquely determined, but in this invention, the distillation can be accomplished favorably with a plate number of 3–20 and at a reflux ratio of up to 5.

In the second distillation tower, a mixture comprising 3,4-DABE in a higher ratio than that in the equilibrium composition of 1,4-DABE and 3,4-DABE or said mixture and acetic acid are distillation-fractionated, and 1,4-DABE with the desired purity is obtained from the tower bottom. The operation conditions for this second distillation tower are not uniquely determined as they are varied depending upon the desired separating conditions, but usually the distillation is performed under reduced pressure or under pressure of up to 10 kg/cm$^2$ (it is desired to apply a pressure of 0.01–3 kg/cm$^2$ considering the polymerizability of diacetoxybutenes), while the temperature is varied depending on the pressure applied, the material composition and the like but it is usually desirable to set the bottom temperature at not more than 220° C., preferably 40°–180° C. The number of plates in the distillation tower and the reflux ratio are also widely variable depending on the mixture composition, the separation conditions, etc., but the distillation can be well accomplished with a plate number of 10–50 and at a reflux ratio of 1–20.

It is a feature of the method of this invention that the mixture comprising 3,4-DABE and 1,4-DABE fractionated by the said operation contains 3,4-DABE in a higher ratio than that in the equilibrium composition of the said substances at the reaction temperature in the isomerization reactor. It is possible to make the concentration of 3,4-DABE in the distillate as very high as at least 90% by weight of diacetoxybutenes, but this requires a distillation system of a larger scale and is disadvantageous in respect of energy. It is also industrially disadvantageous to make the 3,4-DABE concentration in the fractionated mixture not more than 40% by weight of diacetoxybutenes because the isomerization reaction rate is lowered at such a concentration because it is close to the equilibrium composition and also the isomerization throughput itself becomes low. It is, therefore, preferable to keep the proportion of 3,4-DABE in the fractionated mixture within the range of from 40–90% by weight of diacetoxybutenes, particularly from 50–80% by weight of diacetoxybutenes.

The first and second distillation towers used in this invention may be of any suitable type such as packed column, plate column, etc.

The distillate obtained from the second distillation tower is fed to the isomerization reactor in which 3,4-DABE is isomerized into 1,4-DABE with a cation exchange resin as a catalyst as mentioned above.

The isomerization reaction mixture is subjected to separation of the cation exchange resin and then supplied to the second distillation tower. When the reaction mixture contains acetic acid in a high concentration, the whole of said mixture is sent back to the first distillation tower, or the mixture may be divided into two portions, one portion being sent to the first distillation tower and the remainder being circulated into the second distillation tower. As a result, the 1,4-DABE formed by isomerization is obtained from the bottom of the second distillation tower together with 1,4-DABE in the starting material. When acetic acid is present in a large amount in the reaction mixture after the isomerization reaction, a major portion of acetic acid is distillation-fractionated from the top of the first distillation tower together with the starting material while the bottom stream is further distilled in the second distillation tower together with the portion of the isomerization reaction mixture which has been circulated into the second distillation tower, thereby obtaining 1,4-DABE from the bottom of the second distillation tower. When acetic acid is contained in a high concentration in the isomerization reaction mixture, no strict separation of acetic acid and diacetoxybutenes is required in the first distillation tower when considering the subsequent operations, and the amount of the isomerization mixture circulated into the first and second distillation towers after the isomerization reaction may be suitably decided by taking into consideration the acetic acid content, economy and the like.

This invention is further described below with reference to the accompanying drawings, in which:

FIG. 1 is a flow sheet illustrating the method of this invention in which the starting material mixture contains no acetic acid or only a small quantity of acetic acid.

Figure 2:
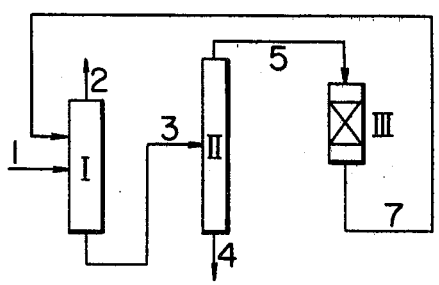
Figure 3:
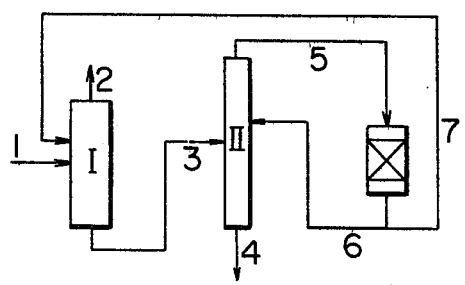

FIGS. 2 and 3 are flow sheets illustrating the method of this invention in which the starting mixture contains a relatively large quantity of acetic acid, FIG. 2 relating to the case where the isomerization reaction solution is entirely circulated into the first distillation tower, and FIG. 3 to the case where the reaction solution is divided into two portions which are circulated into both first and second distillation towers (a modification of FIG. 2).

In the drawings, I designates the first distillation tower, II the second distillation tower, and III the isomerization reactor. Referring first to FIG. 1, the starting material is introduced into the second distillation tower II through a conduit 1. Also introduced into said second distillation tower II through a conduit 6 is the isomerization reaction mixture obtained in the isomerization reactor III. Distillation-fractionated from the top of the tower is a mixture of diacetoxybutenes containing 3,4-DABE in a higher ratio than that in the equilibrium composition of diacetoxybutenes at the isomerization reaction temperature as well as acetic acid if contained, and the distillate is supplied into the isomerization reactor III through a conduit 5. In this reactor, the reaction is carried out in the liquid phase in the presence of a cation exchange resin, and the reaction mixture is circulated into the distillation tower II through the conduit 6. High-purity 1,4-DABE is obtained continuously from the bottom of the tower in an increased yield through a conduit 4.

In FIG. 2, the starting material is introduced into the first distillation tower I through a conduit 1 while the isomerization reaction mixture is supplied to said tower through a conduit 7, where a major amount of the acetic acid is distilled out. The mixture containing the residual acetic acid, 3,4-DABE and 1,4-DABE is withdrawn from the bottom of the tower through a conduit 3 and supplied to the second distillation tower II. In the second distillation tower II, acetic acid and a mixture of diacetoxybutenes containing 3,4-DABE in a higher ratio than that in the equilibrium composition of diacetoxybutenes at the isomerization temperature are distillation-fractionated and sent to the isomerization reactor III through a conduit 5. The isomerization reactor III is filled with a cation exchange resin and the reaction is performed therein in the liquid phase to convert 3,4-DABE into 1,4-DABE. The reaction mixture (containing acetic acid) is forwarded to the first distillation tower through a conduit 7, while the objective product 1,4-DABE is obtained with a high purity continuously from the bottom of the second distillation tower II through a conduit 4.

The system of FIG. 3 is operated in the same manner as the system of FIG. 2, except that a part of the isomerization reaction mixture is circulated into the second distillation tower II through a conduit 6.

Thus, according to the method of this invention, it is possible to produce high-purity 1,4-DABE continuously at a high reaction rate and in a good yield by a very simple process.

This invention is further described below referring to Examples. In the Examples, all "%" is by weight unless otherwise specified.

EXAMPLE 1

To a 300-cc glass autoclave was fed 100 g of a mixed solution comprising 75.0% of 3,4-DABE and 25.0% of 1,4-DABE, and 20 g of a cation exchange resin (a strongly acidic cation exchange resin of the sulfonic acid type comprising a styrene-divinylbenzene copolymer as a matrix which had been converted into the H type; Amberlite 200-C, a trade name of Organo Co., Ltd.) was introduced thereinto, where the mixture was subjected to reaction at 120° C. An analysis of the reaction mixture one hour after the commencement of the reaction showed a 1,4-DABE proportion of 31.0%, and as it reached 40.8% three hours later, the reaction was stopped and the diacetoxybutenes were recovered. The yield was 97.0 g.

EXAMPLE 2

The same procedure as in Example 1 was repeated, except that 40 g of acetic acid was added to effect reaction. When the reaction mixture was analyzed one hour later, the 1,4-DABE proportion in the mixture was 40.0%, and it reached 56.6% three hours later, when the reaction was stopped and the diacetoxybutenes were recovered. The yield was 97.3 g.

EXAMPLE 3

A mixed solution of 90.0% of 3,4-DABE and 10.0% of 1,4-DABE was supplied a glass flow type reaction tube packed with 100 g of the same cation exchange resin as in Example 1 and having an inner diameter of 20 mm and a length of 400 mm, from its bottom at a rate of 100 g/hr and subjected to continuous reaction at 120° C. The reaction mixture effluent from the top of the reaction tube was analyzed to find that the proportion of 1,4-DABE reached 44.6%.

COMPARATIVE EXAMPLE 1

Reaction was carried out in the completely same manner as in Example 2, except that no cation exchange resin was used. An analysis of the reaction mixture three hours after the commencement of the reaction showed no change in the proportion of 1,4-DABE.

EXAMPLE 4

The starting material comprising 1,4-DABE and 3,4-DABE at a molar ratio of 97:3 was supplied continuously to a packed column having an inner diameter of 50 mm and a height of 6 m (packed with 3 mm∅×3 mm porcelain Raschig rings) at a rate of 10 kg/hr, and the column was operated under a pressure of 60 mmHg, at a bottom temperature of 150° C. and at a reflux ratio of 5. A mixture of diacetoxybutenes containing 71% of 3,4-DABE was obtained from the top of the tower, and this mixture was supplied to an isomerization reactor having an inner diameter of 100 mm and a height of 40 cm and packed in five stages with a total of 1.5 kg of the same cation exchange resin as in Example 1, and the mixture was reacted at 120° C. The resultant reaction mixture containing 48% of 3,4-DABE was circulated into said packed column at the rate of 1.5 kg/hr, and this operation was repeated steadily. As a result, a diacetoxybutene mixture containing 99.9% of 1,4-DABE was obtained continuously at a rate of 9.95 kg/hr from the bottom of the packed column.

EXAMPLE 5

The starting material comprising 1,4-DABE and 3,4-DABE in a molar ratio of 97:3 was supplied continuously to a packed column having an inner diameter of 100 mm and a height of 6 m (packed with 3 mm∅×3 mm porcelain Raschig rings) at a rate of 10 kg/hr. Also supplied into said packed column from the isomerization reactor were 1.5 kg/hr of acetic acid and 1.5 kg of a 1:1 mixture of 3,4-DABE and 1,4-DABE, and the column was operated under the following conditions: pressure, 60 mmHg; bottom temperature, 150° C.; reflux ratio, 5.2. From the top of the column, acetic acid and a 73:27 mixture of 3,4-DABE and 1,4-DABE were withdrawn continuously each at a rate of 1.5 kg/hr.

These substances were supplied to an isomerization reactor having an inner diameter of 100 mm and a height of 50 cm and packed in four stages with a total of 0.4 kg of the same cation exchange resin as in Example 1 and subjected to reaction at 120° C. The reaction mixture was circulated into the packed column, and this operation was repeated steadily. Ten hours after the commencement of the reaction, a DABE product containing 99.9% of 1,4-DABE was obtained from the bottom of the column at a rate of 9.9 kg/hr. The same result was obtained even 30 hours after the commencement of the reaction.

EXAMPLE 6

Acetic acid, 3,4-DABE and 1,4-DABE were supplied at rates of 8.5 kg/hr, 0.3 kg/hr and 9.7 kg/hr, respectively, to the first distillation tower having an inner diameter of 55 mm and a height of 1.5 m (packed with 5 mm∅×5 mm porcelain Raschig rings). Also supplied to said tower from the isomerization reactor were acetic acid (1.5 kg/hr) and a mixture of 3,4-DABE (0.72 kg/hr) and 1,4-DABE (0.78 kg/hr). The distillation tower was operated under a pressure of 70 mmHg at a bottom temperature of 148° C. at a reflux ratio of 0.2, and after distillation-fractionating the acetic acid at a rate of 8.5 kg/hr, the bottom stream was fed to the second distillation tower with an inner diameter of 100 mm and a height of 6 m (packed with 3 mm∅×3 mm porcelain Raschig rings), said tower being operated under a pressure of 60 mmHg at a bottom temperature of 150° C. at a reflux ratio of 5.0, whereby acetic acid and a 69:31 mixture of 3,4-DABE and 1,4-DABE were distillation-fractionated each at a rate of 1.5 kg/hr. The distillate was supplied to an isomerization reactor having an inner diameter of 100 mm and a height of 50 cm and packed in four stages with a total of 0.4 kg of the same cation exchange resin as in Example 1 and passed therethrough at 120° C. The reaction mixture comprising 3,4-DABE and 1,4-DABE in a molar ratio of 48:52 was withdrawn and supplied to the first distillation tower, and this operation was repeated steadily. Ten hours after the commencement of the operation, a diacetoxybutene mixture containing 99.9% of 1,4-DABE was obtained from the bottom of the second distillation tower at a rate of 9.9 kg/hr. The same result was obtained even 30 hours after the commencement of the operation.

EXAMPLE 7

Acetic acid, 3,4-DABE and 1,4-DABE were supplied at rates of 8.6 kg/hr, 0.3 kg/hr and 9.7 kg/hr, respectively, to the first distillation tower having an inner diameter of 55 mm and a height of 1.5 m (packed with 5 mm∅×5 mm porcelain Raschig rings). Also supplied to said distillation tower was 67% of the reaction mixture obtained from the isomerization reactor. The distillation tower was operated under a pressure of 70 mmHg at a bottom temperature of 150° C. at a reflux ratio of 0.2, and after distillation-fractionating the acetic acid at a rate of 8.6 kg/hr, the bottom stream was supplied to the second distillation tower having an inner diameter of 100 mm and a height of 6 m packed with 3 mm∅×3 mm porcelain Raschig rings. Also supplied to this second distillation tower was 33% of the isomerization reaction mixture. This distillation tower was operated under a pressure of 60 mmHg at a bottom temperature of 150° C. at a reflux ratio of 5.3, whereby acetic acid and a 33:67 mixture of 3,4-DABE and 1,4-DABE were distillation-fractionated each at a rate of 1.5 kg/hr.

This distillate was supplied to an isomerization reactor having an inner diameter of 100 mm and a height of 50 cm packed in four stages with a total of 0.4 kg of the same cation exchange resin as in Example 1 and passed therethrough at 120° C. The reaction mixture comprising 3,4-DABE and 1,4-DABE in a molar ratio of 47:53 was withdrawn from the bottom of the reactor and circulated into the first and second distillation towers in portions of 67% and 33%, respectively, and this operation was repeated steadily. Ten hours after the commencement of the operation, a diacetoxybutene product containing 99.9% of 1,4-DABE was obtained from the bottom of the second distillation tower. The same result was obtained even 30 hours after the commencement of the operation.

What is claimed is:

1. A method for the isomerization of 3,4-diacetoxybutene-1, comprising:
   contacting the 3,4-diacetoxybutene-1 with a cation exchange resin in the presence of from 0.1–2000 parts by weight acetic acid per 100 parts by weight 3,4-diacetoxybutene-1, thereby isomerizing the same to 1,4-diacetoxybutene-2.

2. A method for producing 1,4-diacetoxybutene-2, which comprises: supplying a mixture comprising 1,4-diacetoxybutene-2, 3,4-diacetoxybutene-1 and acetic acid to a first distillation tower, distillation-fractionating a major amount of acetic acid from the top of the tower, supplying to a second distillation tower a mixture comprising 1,4-diacetoxybutene-2, 3,4-diacetoxybutene-1 and acetic acid obtained from the bottom of the tower, distillation-fractionating the acetic acid and a mixture of diacetoxybutenes comprising 3,4-diacetoxybutene-1 in a higher ratio than that in the equilibrium composition of the diacetoxybutenes at the isomerization temperature, supplying the distillate to an isomerization reactor containing a cation exchange resin such that from 0.1–2000 parts by weight acetic acid is present per 100 parts by weight 3,4-diacetoxybutene-1 to effect isomerization in the liquid phase, circulating the whole of the isomerization reaction mixture obtained to the first distillation tower or supplying a part of said reaction mixture to the second distillation tower and circulating the remainder into the first distillation tower while continuously taking out high-purity 1,4-diacetoxybutene-2 from the bottom of the second distillation tower.

3. The method of claim 2, wherein the operating conditions of the first distillation tower are such that the pressure is reduced to a pressure of 10 kg/cm$^2$, the bottom temperature is up to 220° C., the number of plates is 3–20 and the reflux ratio is up to 5; the operating conditions of the second distillation tower are such that the pressure is reduced to a pressure of 10 kg/cm$^2$, the bottom temperature is up to 220° C., the number of plates is 10–50 and the reflux ratio is 1–20; and the proportion of 3,4-diacetoxybutene-1 in the distillate which is supplied to the isomerization reaction is 40–90% by weight of diacetoxybutenes.

4. The method of claim 1, wherein the cation exchange resin is a strongly acidic one.

5. The method of claim 4, wherein the cation exchange resin is a strongly acidic cation exchange resin of the sulfonic acid type comprising a styrene-divinylbenzene copolymer as a matrix.

6. The method of claim 1, wherein the proportion of the cation exchange resin to the 3,4-diacetoxybutene-1 is 0.001–10% by weight.

7. The method of claim 2, wherein the cation exchange resin is a strongly acidic one.

8. The method of claim 7, wherein the cation exchange resin is a strongly acidic cation exchange resin of the sulfonic acid type comprising a styrene-divinylbenzene copolymer as a matrix.

9. The method of claim 2, wherein the proportion of the cation exchange resin to the 3,4-diacetoxybutene-1 is 0.001–10% by weight.

* * * * *